(12) United States Patent
Allen et al.

(10) Patent No.: US 6,204,063 B1
(45) Date of Patent: Mar. 20, 2001

(54) PLANT GLYCOLYSIS AND RESPIRATION ENZYMES

(75) Inventors: Stephen M. Allen; Jian-Ming Lee, both of Wilmington, DE (US); Jonathan E. Lightner, Airville; Joan T. Odell, Unionville, both of PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/268,364

(22) Filed: Mar. 15, 1999

Related U.S. Application Data

(60) Provisional application No. 60/079,387, filed on Mar. 26, 1998.

(51) Int. Cl.[7] ............................. C12N 5/04; C12N 15/82; C12N 15/29; C12N 15/74; A01H 5/00
(52) U.S. Cl. ........................ 435/468; 435/419; 435/69.1; 435/485; 435/486; 435/487; 435/488; 435/252.3; 536/23.1; 536/23.2; 536/23.6
(58) Field of Search .................................. 435/468, 419, 435/69.1, 252.3, 488, 485, 486, 487; 536/23.1, 23.2, 23.6

(56) References Cited

U.S. PATENT DOCUMENTS 5,387,756 * 2/1995 Burrell et al. ........................ 800/205

OTHER PUBLICATIONS

NCBI General Identifier No. 3170230.
NCBI General Identifier No. 3309583.
NCBI General Identifier No. 2506091.
Algarier et al., Biochemical and Biophysical Research Comm., (1988), 153 No. 1, 328–333.
Nobrega et al., EMBO J., (1992), 11 No. 11, 3821–3829.
Folsch et al., EMBO J., (1996), 15, 479–487.

* cited by examiner

Primary Examiner—David T. Fox
Assistant Examiner—Medina A. Ibrahim

(57) ABSTRACT

This invention relates to an isolated nucleic acid fragment encoding a glycolysis or respiration protein. The invention also relates to the construction of a chimeric gene encoding all or a portion of the glycolysis or respiration protein, in sense or antisense orientation, wherein expression of the chimeric gene results in production of altered levels of the glycolysis or respiration protein in a transformed host cell.

9 Claims, 1 Drawing Sheet

FIGURE 1

```
                        1                                                           60
SEQ ID NO:21             MSDKPIDIQYDKQATPNLSGVITPPTNETGNDSVREKLSKLVGDAMSNNPYFAAGGGLMI
SEQ ID NO:4  (gi 2506091) ARGNAERRSY-----RLT---------------------FHRRHRALV-----ENAY---

61                                                          120
SEQ ID NO:21             LGTGLAVARSGIIKASRVLYRQMIVDLEIQSKDKSYAWFLTWMAKHPQRVSRHLSVRTNY
SEQ ID NO:4  (gi 2506091) LPHVLAEGRAVTVRNRQ---------------------------------RRL-------

121                                                         180
SEQ ID NO:21             IQHDNGSVSTKFSLVPGPGNHWIRYKGAFILIKRERSAKMIDIANGSPFETVTLTTLYRD
SEQ ID NO:4  (gi 2506091) -----------------FTNNPSADWSAYDDARV--------------------------

181                                                         240
SEQ ID NO:21             KHLFDDILNEAKDIALKTTEGKTVIYTSFGPEWR--KFGQPKAKRMLPSVILDSGIKEGI
SEQ ID NO:4  (gi 2506091) -----------------------------WSHVKLEHPST---FATLAMDPVRKQEI--

241                                                         300
SEQ ID NO:21             LDDVYDFMKNGKWYSDRGIPYRRGYLLYGPPGSGKTSFIQALAGELDYNICILNLSENNL
SEQ ID NO:4  (gi 2506091) IDDLDMFRDGKEYYASVGKAWKRGYLLFGPPGTGKSTMIAAMANFLDYGVYDLELTAVK- 301                                                         360
SEQ ID NO:21             TDDRLNHLMNNMPERSILLLEDIDAAFNKRSQTGEQGFHSSVTFSGLLNALDGVTSSEET
SEQ ID NO:4  (gi 2506091) SNTELRRLFIETTGKSIIVIEDIDCSID-------------------LTGKRKKKKK---

361                                                         420
SEQ ID NO:21             ITFMTTNHPEKLDAAIMRPGRIDYKVFVGNATPYQVEKMFMKFYPGETDICKKFVNSVKE
SEQ ID NO:4  (gi 2506091) -----DKKKKKMTPPWARDD------------------DEELMWRR-------DVTKS--

421                           458
SEQ ID NO:21             LDITVSTAQLQGLFVMNKDAPHDALKMVSSLRNANHIF
SEQ ID NO:4  (gi 2506091) -------------------------------------
```

PLANT GLYCOLYSIS AND RESPIRATION ENZYMES

This application claims the benefit of U.S. Provisional Application No. 60/079,387, filed Mar. 26, 1998.

FIELD OF THE INVENTION

This invention is in the field of plant molecular biology. More specifically, this invention pertains to nucleic acid fragments encoding proteins involved in glycolysis and respiration in plants and seeds.

BACKGROUND OF THE INVENTION

Glycolysis is the main pathway for carbohydrate catabolism. It is a process in which monosaccharides are broken down to pyruvic acid, two molecules of which are formed per monosaccharide residue. In plants D-glucose and D-fructose are the main monosaccharides catabolized by glycolysis although other monosaccharides that can be converted to glucose or fructose can be handled by this catabolic pathway. In cells where photosynthesis is not taking place glycolysis is a key metabolic component of the respiratory process which generates energy in the form of ATP. Typically the cells of germinating seedlings and non-photosynthetic cells of mature plants utilize this metabolic pathway. The glycolytic pathway is controlled in part by the potent allosteric regulator fructose-2,6-bisphosphate (F2,6P). This regulatory molecule activates the enzymatic activity of phosphofructosekinase (PFK) which stimulates the flow of carbon through the glycolytic pathway to pyruvate. PFK plays a central role in the control of glycolysis because it catalyzes one of the pathway's rate-determining reactions. F2,6P also inhibits the activity of fructose bisphosphatase (FBPase) which stimulates the flow of carbon through gluconeogenesis, to form glucose. The concentration of F2,6P in the cell depends on the action of 6-phosphofructo 2-kinase/fructose 2,6-bisphosphatase (PFK-2/FBPase). The formation and degradation of F2,6P is catalyzed by PFK-2 and FBPase-2, two enzyme activities that occur on different domains of the same protein molecule (Algaier, J. et al. (1988) *Biochem Biophys Res Commun* 153(1):328–333). Thus, 6-phosphofructo 2-kinase/fructose 2,6-bisphosphatase is a key regulatory enzyme that controls carbon flux through glycolysis vs. gluconeogenesis. Because PFK-2/FBPase regulates the abundance of a key allosteric regulator, manipulating the activity of this enzyme either by controlling expression or by directed mutagenesis could be used to control carbon flux through the glycolytic of gluconeogenic pathways. This could be very important in bioprocessing in plants.

Respiration (aerobic metabolism) takes place in the mitochondria in most eukaryotes. The ubiquinol-cytochrome C reductase (bc1) complex is an important component of the mitochondrial electron transport system. The BCS1 gene encodes a product that has been shown to be necessary for the expression of the Rieske iron-sulfur protein a component of the bc1 complex (Nobrega, F. G. et al. (1992) *EMBO* 11:3821–3829). By controlling the expression of BCS1 it may be possible to modulate the level of the Rieske iron-sulfur protein in plant cells which it turn would regulate the amount of functional ubiquinol-cytochrome C reductase complexes in mitochondria.

Few of the genes encoding the 6-phosphofructo 2-kinase/fructose 2,6-bisphosphatase and BCS1 proteins in corn, Momordica, rice and wheat, have been isolated and sequenced. For example, no corn, Momordica, rice or wheat genes have been reported for 6-phosphofructo 2-kinase/fructose 2,6-bisphosphatase and no plant genes have been reported for BCS1. Accordingly, the availability of nucleic acid sequences encoding all or a portion of these proteins would facilitate studies to better understand carbon flux and respiration, provide genetic tools for the manipulation of these metabolic pathways, and provide a means to control glycolysis and respiration in plant cells.

SUMMARY OF THE INVENTION

The instant invention relates to isolated nucleic acid fragments encoding proteins involved in glycolysis and respiration. Specifically, this invention concerns an isolated nucleic acid fragment encoding a BCS1 or 6-phosphofructo 2-kinase/fructose 2,6-bisphosphatase protein. In addition, this invention relates to a nucleic acid fragment that is complementary to the nucleic acid fragment encoding a BCS1 or 6-phosphofructo 2-kinase/fructose 2,6-bisphosphatase protein.

An additional embodiment of the instant invention pertains to a polypeptide encoding all or a substantial portion of a protein involved in glycolysis or respiration selected from the group consisting of BCS1 and 6-phosphofructo 2-kinase/fructose 2,6-bisphosphatase.

In another embodiment, the instant invention relates to a chimeric gene encoding a BCS1 or 6-phosphofructo 2-kinase/fructose 2,6-bisphosphatase protein, or to a chimeric gene that comprises a nucleic acid fragment that is complementary to a nucleic acid fragment encoding a BCS1 or 6-phosphofructo 2-kinase/fructose 2,6-bisphosphatase protein, operably linked to suitable regulatory sequences, wherein expression of the chimeric gene results in production of levels of the encoded protein in a transformed host cell that is altered (i.e., increased or decreased) from the level produced in an untransformed host cell.

In a further embodiment, the instant invention concerns a transformed host cell comprising in its genome a chimeric gene encoding a BCS1 or 6-phosphofructo 2-kinase/fructose 2,6-bisphosphatase protein, operably linked to suitable regulatory sequences. Expression of the chimeric gene results in production of altered levels of the encoded protein in the transformed host cell. The transformed host cell can be of eukaryotic or prokaryotic origin, and include cells derived from higher plants and microorganisms. The invention also includes transformed plants that arise from transformed host cells of higher plants, and seeds derived from such transformed plants.

An additional embodiment of the instant invention concerns a method of altering the level of expression of a BCS1 or 6-phosphofructo 2-kinase/fructose 2,6-bisphosphatase protein in a transformed host cell comprising: a) transforming a host cell with a chimeric gene comprising a nucleic acid fragment encoding a BCS1 or 6-phosphofructo 2-kinase/fructose 2,6-bisphosphatase protein; and b) growing the transformed host cell under conditions that are suitable for expression of the chimeric gene wherein expression of the chimeric gene results in production of altered levels of BCS1 or 6-phosphofructo 2-kinase/fructose 2,6-bisphosphatase protein in the transformed host cell.

An addition embodiment of the instant invention concerns a method for obtaining a nucleic acid fragment encoding all or a substantial portion of an amino acid sequence encoding a BCS1 or 6-phosphofructo 2-kinase/fructose 2,6-bisphosphatase protein.

BRIEF DESCRIPTION OF THE DRAWINGS AND SEQUENCE DESCRIPTIONS

The invention can be more fully understood from the following detailed description and the accompanying drawings and Sequence Listing which form a part of this application.

FIG. 1 presents an alignment of the amino acid sequence set forth in SEQ ID NO:4 and the *Saccharomyces cerevisiae* BCS1 protein (NCBI Identifier No. gi 2506091; SEQ ID NO:21).

The following sequence descriptions and Sequence Listing attached hereto comply with the rules governing nucleotide and/or amino acid sequence disclosures in patent applications as set forth in 37 C.F.R. §1.821–1.825.

SEQ ID NO:1 is the nucleotide sequence comprising a contig assembled from the cDNA inserts in clones cr1n.pk0185.g6, p0010.cbpca28r, p0126.cn1cr73r, p0126.cnldc60r and cpf1c.pk009.116 encoding a portion of a corn BCS1 protein.

SEQ ID NO:2 is the deduced amino acid sequence of a portion of a BCS1 protein derived from the nucleotide sequence of SEQ ID NO:1.

SEQ ID NO:3 is the nucleotide sequence comprising a portion of the cDNA insert in clone rr1.pk0025.d4 encoding a portion of a rice BCS1 protein.

SEQ ID NO:4 is the deduced amino acid sequence of a portion of a BCS1 protein derived from the nucleotide sequence of SEQ ID NO:3.

SEQ ID NO:5 is the nucleotide sequence comprising a portion of the cDNA insert in clone rr1.pk0026.e10 encoding a portion of a rice BCS1 protein.

SEQ ID NO:6 is the deduced amino acid sequence of a portion of a BCS1 protein derived from the nucleotide sequence of SEQ ID NO:5.

SEQ ID NO:7 is the nucleotide sequence comprising a portion of the cDNA insert in clone s12.pk127.m2 encoding a portion of a soybean BCS1 protein.

SEQ ID NO:8 is the deduced amino acid sequence of a portion of a BCS1 protein derived from the nucleotide sequence of SEQ ID NO:7.

SEQ ID NO:9 is the nucleotide sequence comprising a portion of the cDNA insert in clone wre1n.pk0059.e1 encoding a portion of a wheat BCS1 protein.

SEQ ID NO:10 is the deduced amino acid sequence of a portion of a BCS1 protein derived from the nucleotide sequence of SEQ ID NO:9.

SEQ ID NO:11 is the nucleotide sequence comprising a portion of the cDNA insert in clone cs1.pk0039.d2 encoding a portion of a corn 6-phosphofructo 2-kinase/fructose 2,6-bisphosphatase protein.

SEQ ID NO:12 is the deduced amino acid sequence of a portion of a 6-phosphofructo 2-kinase/fructose 2,6-bisphosphatase protein derived from the nucleotide sequence of SEQ ID NO:11.

SEQ ID NO:13 is the nucleotide sequence comprising a portion of the cDNA insert in clone fds.pk0026.a2 encoding a portion of a Momordica 6-phosphofructo 2-kinase/fructose 2,6-bisphosphatase protein.

SEQ ID NO:14 is the deduced amino acid sequence of a portion of a 6-phosphofructo 2-kinase/fructose 2,6-bisphosphatase protein derived from the nucleotide sequence of SEQ ID NO:13.

SEQ ID NO:15 is the nucleotide sequence comprising a contig assembled from the cDNA inserts in clones rls6.pk0007.b6, rds2c.pk005.d2, rlr6.pk0085.b4 and rls48.pk0013.b4 encoding a portion of a rice 6-phosphofructo 2-kinase/fructose 2,6-bisphosphatase protein.

SEQ ID NO:16 is the deduced amino acid sequence of a portion of a 6-phosphofructo 2-kinase/fructose 2,6-bisphosphatase protein derived from the nucleotide sequence of SEQ ID NO:15.

SEQ ID NO:17 is the nucleotide sequence comprising a portion of the cDNA insert in clone src2c.pk003.p13 encoding a portion of a soybean 6-phosphofructo 2-kinase/fructose 2,6-bisphosphatase protein.

SEQ ID NO:18 is the deduced amino acid sequence of a portion of a 6-phosphofructo 2-kinase/fructose 2,6-bisphosphatase protein derived from the nucleotide sequence of SEQ ID NO:17.

SEQ ID NO:19 is the nucleotide sequence comprising a contig assembled from the cDNA inserts in clones wlsu2.pk029.111 and wkm2c.pk006.h13 encoding a portion of a wheat 6-phosphofructo 2-kinase/fructose 2,6-bisphosphatase protein.

SEQ ID NO:20 is the deduced amino acid sequence of a portion of a 6-phosphofructo 2-kinase/fructose 2,6-bisphosphatase protein derived from the nucleotide sequence of SEQ ID NO:19.

SEQ ID NO:21 is the amino acid sequence of the *Saccharomyces cerevisiae* BCS1 sequence set forth in NCBI Identifier No. gi 2506091.

The Sequence Listing contains the one letter code for nucleotide sequence characters and the three letter codes for amino acids as defined in conformity with the IUPAC-IUBMB standards described in *Nucleic Acids Research* 13:3021–3030 (1985) and in the *Biochemical Journal* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA. As used herein, "contig" refers to an assemblage of overlapping nucleic acid sequences to form one contiguous nucleotide sequence. For example, several DNA sequences can be compared and aligned to identify common or overlapping regions. The individual sequences can then be assembled into a single contiguous nucleotide sequence.

As used herein, "substantially similar" refers to nucleic acid fragments wherein changes in one or more nucleotide bases results in substitution of one or more amino acids, but do not affect the functional properties of the protein encoded by the DNA sequence.

"Substantially similar" also refers to nucleic acid fragments wherein changes in one or more nucleotide bases does not affect the ability of the nucleic acid fragment to mediate alteration of gene expression by antisense or co-suppression technology. "Substantially similar" also refers to modifications of the nucleic acid fragments of the instant invention such as deletion or insertion of one or more nucleotides that do not substantially affect the functional properties of the resulting transcript vis-a-vis the ability to mediate alteration of gene expression by antisense or co-suppression technology or alteration of the functional properties of the resulting protein molecule. It is therefore understood that the invention encompasses more than the specific exemplary sequences.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a gene which result in the production of a chemically equivalent amino acid at a given site, but do not effect the functional properties of the encoded protein, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the protein molecule would also not be expected to alter the activity of the protein. Each of the proposed modifications is well within the routine skill in the art, as is determination of retention of biological activity of the encoded products.

Moreover, substantially similar nucleic acid fragments may also be characterized by their ability to hybridize, under stringent conditions (0.1×SSC, 0.1% SDS, 65° C.), with the nucleic acid fragments disclosed herein.

Substantially similar nucleic acid fragments of the instant invention may also be characterized by the percent similarity of the amino acid sequences that they encode to the amino acid sequences disclosed herein, as determined by algorithms commonly employed by those skilled in this art. Preferred are those nucleic acid fragments whose nucleotide sequences encode amino acid sequences that are 80% similar to the amino acid sequences reported herein. More preferred nucleic acid fragments encode amino acid sequences that are 90% similar to the amino acid sequences reported herein. Most preferred are nucleic acid fragments that encode amino acid sequences that are 95% similar to the amino acid sequences reported herein. Sequence alignments and percent similarity calculations were performed using the Megalign program of the LASARGENE bioinformatics computing suite (DNASTAR Inc., Madison, Wis.). Multiple alignment of the sequences was performed using the Clustal method of alignment (Higgins, D. G. and Sharp, P. M. (1989) *CABIOS.* 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises enough of the amino acid sequence of a polypeptide or the nucleotide sequence of a gene to afford putative identification of that polypeptide or gene, either by manual evaluation of the sequence by one skilled in the art, or by computer-automated sequence comparison and identification using algorithms such as BLAST (Basic Local Alignment Search Tool; Altschul, S. F., et al., (1993) *J. Mol. Biol.* 215:403–410; see also www.ncbi.nlm.nih.gov/BLAST/). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20–30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12–15 bases may be used as amplification primers in PCR in order to obtain a particular nucleic acid fragment comprising the primers. Accordingly, a "substantial portion" of a nucleotide sequence comprises enough of the sequence to afford specific identification and/or isolation of a nucleic acid fragment comprising the sequence. The instant specification teaches partial or complete amino acid and nucleotide sequences encoding one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment that encodes all or a substantial portion of the amino acid sequence encoding the BCS1 and 6-phosphofructo 2-kinase/fructose 2,6-bisphosphatase proteins as set forth in SEQ ID NOs:2, 4, 6, 8, 10, 12, 14, 16, 18 and 20. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a DNA sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". New promoters of various types useful in plant cells are constantly being discovered; numerous examples may be found in the compilation by Okamuro and Goldberg, (1989) *Biochemistry of Plants* 15:1–82. It is further recognized that since in most cases the exact boundaries of regulatory sequences have not been completely defined, DNA fragments of different lengths may have identical promoter activity.

The "translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D. (1995) *Molecular Biotechnology* 3:225).

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065, incorporated herein by reference). The complementarity of an antisense RNA may be with any part of the specific gene transcript, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product (s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels, J. J., (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 143:277) and particle-accelerated or "gene gun" transformation technology (Klein et al. (1987) *Nature* (London) 327:70–73; U.S. Pat. No. 4,945,050, incorporated herein by reference).

Standard recombinant DNA and molecular cloning techniques used herein are well known in the art and are described more fully in Sambrook, J., Fritsch, E. F. and Maniatis, T. *Molecular Cloning: A Laboratory Manual;* Cold Spring Harbor Laboratory Press: Cold Spring Harbor, 1989 (hereinafter "Maniatis").

Nucleic acid fragments encoding at least a portion of several proteins involved in glycolysis and respiration have been isolated and identified by comparison of random plant cDNA sequences to public databases containing nucleotide and protein sequences using the BLAST algorithms well known to those skilled in the art. Table 1 lists the proteins that are described herein, and the designation of the cDNA clones that comprise the nucleic acid fragments encoding these proteins.

labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al., (1988) *PNAS USA* 85:8998) to generate cDNAs by using PCR to amplify copies of the region between a single point in the transcript

TABLE 1

Glycolysis and Respiration Proteins

| Enzyme | Clone | Plant |
| --- | --- | --- |
| BCS1 | cr1n.pk0185.g6 | Corn |
|  | p0010.cbpca28r | Corn |
|  | p0126.cn1cr73r | Corn |
|  | p0126.cn1dc60r | Corn |
|  | cpf1c.pk009.l16 | Corn |
|  | rr1.pk0025.d4 | Rice |
|  | rr1.pk0026.e10 | Rice |
|  | sl2.pk127.m2 | Soybean |
|  | wre1n.pk0059.e1 | Wheat |
| 6-phosphofructo 2-kinase/fructose 2,6-bisphosphatase | cs1.pk0039.d2 | Corn |
|  | fds.pk0026.a2 | Momordica |
|  | rls6.pk0007.b6 | Rice |
|  | rds2c.pk005.d2 | Rice |
|  | rlr6.pk0085.b4 | Rice |
|  | r1s48.pk0013.b4 | Rice |
|  | src2c.pk003.p13 | Soybean |
|  | wlsu2.pk029.l11 | Wheat |
|  | wkm2c.pk006.h13 | Wheat |

The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other BCS1 or 6-phosphofructo 2-kinase/fructose 2,6-bisphosphatase proteins, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al., (1989) *PNAS USA* 86:5673; Loh et al., (1989) *Science* 243:217). Products generated by the 3' and 5' RACE procedures can be combined to generate full-length cDNAs (Frohman, M. A. and Martin, G. R., (1989) *Techniques* 1:165).

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner, R. A. (1984) *Adv. Immunol.* 36:1; Maniatis).

The nucleic acid fragments of the instant invention may be used to create transgenic plants in which the disclosed BCS1 or 6-phosphofructo 2-kinase/fructose 2,6-bisphosphatase proteins are present at higher or lower levels than normal or in cell types or developmental stages in which they are not normally found. This would have the effect of modulating respiration or altering the level of carbon flux in glycolysis in those cells.

Overexpression of the BCS1 or 6-phosphofructo 2-kinase/fructose 2,6-bisphosphatase proteins of the instant invention may be accomplished by first constructing a chimeric gene in which the coding region is operably linked to a promoter capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant chimeric gene can then constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., (1985) *EMBO J.* 4:2411–2418; De Almeida et al., (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant glycolysis and respiration proteins to different cellular compartments, or to facilitate its secretion from the cell. It is thus envisioned that the chimeric gene described above may be further supplemented by altering the coding sequence to encode a BCS1 or 6-phosphofructo 2-kinase/fructose 2,6-bisphosphatase protein with appropriate intracellular targeting sequences such as transit sequences (Keegstra, K. (1989) *Cell* 56:247–253), signal sequences or sequences encoding endoplasmic reticulum localization (Chrispeels, J. J., (1991) *Ann. Rev. Plant Phys. Plant Mol. Biol.* 42:21–53), or nuclear localization signals (Raikhel, N. (1992) *Plant Phys.* 100:1627–1632) added and/or with targeting sequences that are already present removed. While the references cited give examples of each of these, the list is not exhaustive and more targeting signals of utility may be discovered in the future.

It may also be desirable to reduce or eliminate expression of genes encoding BCS1 or 6-phosphofructo 2-kinase/fructose 2,6-bisphosphatase proteins in plants for some applications. In order to accomplish this, a chimeric gene designed for co-suppression of the instant glycolysis and respiration proteins can be constructed by linking a gene or gene fragment encoding a BCS1 or 6-phosphofructo 2-kinase/fructose 2,6-bisphosphatase protein to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

The instant BCS1 or 6-phosphofructo 2-kinase/fructose 2,6-bisphosphatase proteins (or portions thereof) may be produced in heterologous host cells, particularly in the cells of microbial hosts, and can be used to prepare antibodies to the these proteins by methods well known to those skilled in the art. The antibodies are useful for detecting BCS1 or 6-phosphofructo 2-kinase/fructose 2,6-bisphosphatase proteins in situ in cells or in vitro in cell extracts. Preferred heterologous host cells for production of the instant BCS1 or 6-phosphofructo 2-kinase/fructose 2,6-bisphosphatase proteins are microbial hosts. Microbial expression systems and expression vectors containing regulatory sequences that direct high level expression of foreign proteins are well known to those skilled in the art. Any of these could be used to construct a chimeric gene for production of the instant BCS1 or 6-phosphofructo 2-kinase/fructose 2,6-bisphosphatase proteins. This chimeric gene could then be introduced into appropriate microorganisms via transformation to provide high level expression of the encoded glycolysis or respiration protein. An example of a vector for high level expression of the instant BCS1 or 6-phosphofructo 2-kinase/fructose 2,6-bisphosphatase proteins in a bacterial host is provided (Example 7).

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et at., (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein, D. et al., (1980) *Am. J. Hum. Genet.* 32:314–331).

The production and use of plant gene-derived probes for use in genetic mapping is described in R. Bernatzky, R. and Tanksley, S. D. (1986) *Plant Mol. Biol. Reporter* 4(1):37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel, J. D., et al., In: *Nonmammalian Genomic Analysis: A Practical Guide,* Academic press 1996, pp. 319–346, and references cited therein).

In another embodiment, nucleic acid probes derived from the instant nucleic acid sequences may be used in direct fluorescence in situ hybridization (FISH) mapping (Trask, B. J. (1991) *Trends Genet.* 7:149–154). Although current methods of FISH mapping favor use of large clones (several to several hundred KB; see Laan, M. et al. (1995) *Genome Research* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian, H. H. (1989) *J. Lab. Clin. Med.* 114(2):95–96), polymorphism of PCR-amplified fragments (CAPS; Sheffield, V. C. et al. (1993) *Genomics* 16:325–332), allele-specific ligation (Landegren, U. et al. (1988) *Science* 241:1077–1080), nucleotide extension reactions (Sokolov, B. P. (1990) *Nucleic Acid Res.* 18:3671), Radiation Hybrid Mapping (Walter, M. A. et al. (1997) *Nature Genetics* 7:22–28) and Happy Mapping (Dear, P. H. and Cook, P. R. (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer, (1989) *Proc. Natl. Acad. Sci USA* 86:9402; Koes et al., (1995) *Proc. Natl. Acad. Sci USA* 92:8149; Bensen et al., (1995) *Plant Cell* 7:75). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the BCS1 or 6-phosphofructo 2-kinase/fructose 2,6-bisphosphatase protein. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding a BCS1 or 6-phosphofructo 2-kinase/fructose 2,6-bisphosphatase protein can be identified and obtained. This mutant plant can then be used to determine or confirm the natural function of the BCS1 or 6-phosphofructo 2-kinase/fructose 2,6-bisphosphatase protein gene product.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries; Isolation and Sequencing of cDNA Clones cDNA libraries representing mRNAs from various corn, Momordica, rice, soybean and wheat tissues were prepared. The characteristics of the libraries are described below.

TABLE 2 cDNA Libraries from Corn, Momordica, Rice, Soybean and Wheat

| Library | Tissue | Clone |
|---|---|---|
| cpf1c | Corn pooled BMS treated with chemicals related to protein synthesis** | cpf1c.pk009.116 |
| cr1n | Corn root from 7 day seedlings grown in light* | cr1n.pk0185.g6 |
| cs1 | Corn leaf; sheath 5 wk old plant | cs1.pk0039.d2 |
| fds | *Momordica charantia* developing seed | fds.pk0026.a2 |
| p0010 | Corn log phase suspension cells (BMS) treated with A23187 to induce mass apoptosis**** | p0010.cbpca28r |
| p0126 | Corn, night harvested leaf tissue; V8–V10*** | p0126.cn1cr73r p0126.cnldc60r |
| rds2c | Rice developing seeds in the middle of the plant. | rds2c.pk005.d2 |
| rls6 | Rice leaf, 15 day after germination, 6 hrs after infection of *Magaporthe grisea* strain 4360-R-67 (avr2-yamo); Susceptible | rls6.pk0007.b6 rlr6.pk0085.b4 |
| rls48 | Rice leaf. 15 days after germination, 48 hours after infection of strain *Magaporthe grisea* 4360-R-67 (avr2-yarno); Susceptible | rls48.pk0013.b4 |
| rr1 | Rice root of two week old developing seedling | rr1.pk0025.d4 rr1.pk0026.e10 |
| sl2 | Soybean two week old developing seedlings treated with 2.5 ppm chlorimuron | sl2.pk127.m2 |
| src2c | Soybean 8 day old root inoculated with eggs of cyst nematode *Heterodera glycines* (Race 1) for 4 days | src2c.pk003.p13 |
| wkm2c | Wheat kernel malted 55 hours at 22° C. | wkm2c.pk006.h13 |

TABLE 2-continued cDNA Libraries from Corn, Momordica, Rice, Soybean and Wheat

| Library | Tissue | Clone |
|---|---|---|
| wlsu | Wheat seedlings 8 hr after fungicide***** treatment, subtracted with cDNAs from wheat seedlings 0 hr after inoculation with *Erysiphe graminis f. sp tritici* | wlsu2.pk029.l11 |
| wre1n | Wheat root; 7 day old etiolated seedling* | wre1n.pk0059.e1 |

*These libraries were normalized essentially as described in U.S. Pat. No. 5,482,845
***V8–V10 refer to stages of corn growth. The descriptions can be found in "How a Corn Plant Develops" Special Report No. 48, Iowa State University of Science and Technology Cooperative Extension Service Ames, Iowa, Reprinted February 1996.
****A23187 is commercially available from Calbiochem-Noavbiochem Corp.
*****Application of 6-iodo-2-propoxy-3-propyl-4(3H)-quinazolinone; synthesis and methods of using this compound are described in USSN 08/545,827, incorporated herein by reference.

cDNA libraries were prepared in Uni-ZAP™ XR vectors according to the manufacturer's protocol (Stratagene Cloning Systems, La Jolla, Calif.). Conversion of the Uni-ZAP™ XR libraries into plasmid libraries was accomplished according to the protocol provided by Stratagene. Upon conversion, cDNA inserts were contained in the plasmid vector pBluescript. cDNA inserts from randomly picked bacterial colonies containing recombinant pBluescript plasmids were amplified via polymerase chain reaction using primers specific for vector sequences flanking the inserted cDNA sequences or plasmid DNA was prepared from cultured bacterial cells. Amplified insert DNAs or plasmid DNAs were sequenced in dye-primer sequencing reactions to generate partial cDNA sequences (expressed sequence tags or "ESTs"; see Adams, M. D. et al., (1991) *Science* 252:1651). The resulting ESTs were analyzed using a Perkin Elmer Model 377 fluorescent sequencer.

Example 2

Identification of cDNA Clones

ESTs encoding glycolysis and respiration proteins were identified by conducting BLAST (Basic Local Alignment Search Tool; Altschul, S. F., et al., (1993) *J. Mol. Biol.* 215:403–410; see also www.ncbi.nlm.nih.gov/BLAST/) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish, W. and States, D. J. (1993) *Nature Genetics* 3:266–272 and Altschul, Stephen F., et al. (1997) *Nucleic Acids Res.* 25:3389–3402) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding BCS1 Proteins

The BLASTX search using the EST sequences from clones cr1n.pk0185.g6, p0010.cbpca28r, p0126.cn1cr73r, p0126.cn1dc60r, cpf1c.pk009.116, rr1.pk0026.e10, s12.pk127.m2 and wre1n.pk0059.e1 revealed similarity of the proteins encoded by the cDNAs to BCS1 protein from *Saccharomyces cerevisiae* (NCBI Identifier No. gi 2506091).

A BLASTP search using the amino acid sequence encoded by the cDNA from clone rr1.pk0025.d4 revealed similarity of the encoded protein to BCS1 protein from *Saccharomyces cerevisiae* (NCBI Identifier No. gi 2506091).

In the process of comparing the ESTs it was found that corn clones cr1n.pk0185.g6, p0010.cbpca28r, p0126.cn1cr73r, p0126.cn1dc60r and cpf1c.pk009.116 had overlapping regions of homology. Using this homology it was possible to align the ESTs and assemble a contig encoding a unique corn BCS1 protein. The BLAST results for the corn contig and each of the ESTs are shown in Table 3:

TABLE 3

BLAST Results for Clones Encoding Polypeptides Homologous to *Saccharomyces cerevisiae* BCS1 Protein

| Clone | BLAST pLog Score |
|---|---|
| Contig composed of: | 23.00 |
| cr1n.pk0185.g6 | |
| p0010.cbpca28r | |
| p0126.cn1cr73r | |
| p0126.cn1dc60r | |
| cpf1c.pk009.116 | |
| rr1.pk0025.d4 | 10.30 |
| rr1.pk0026.e10 | 13.00 |
| s12.pk127.m2 | 9.10 |
| wre1n.pk0059.e1 | 10.50 |

The sequence of the corn contig composed of clones cr1n.pk0185.g6, p0010.cbpca28r, p0126.cn1cr73r, p0126.cn1dc60r and cpf1c.pk009.116 is shown in SEQ ID NO:1; the deduced amino acid sequence of this contig, which represents 49% of the protein (middle region), is shown in SEQ ID NO:2.

The sequence of the entire cDNA insert in clone rr1.pk0025.d4 was determined and is shown in SEQ ID NO:3; the deduced amino acid sequence of this cDNA, which represents 50% of the protein (C-terminal region), is shown in SEQ ID NO:4. FIG. 1 presents an alignment of the amino acid sequence set forth in SEQ ID NO:4 and the *Saccharomyces cerevisiae* sequence. A calculation of the percent similarity of the amino acid sequence set forth in SEQ ID NO:4 and the *Saccharomyces cerevisiae* sequence (using the Clustal Algorithm) revealed that the protein encoded by the cDNA insert in clone rr1.pk0025.d4 is 20% similar to the *Saccharomyces cerevisiae* BCS1 protein.

The sequence of a portion of the cDNA insert from clone rr1.pk0026.e10 is shown in SEQ ID NO:5; the deduced amino acid sequence of this cDNA, which represents 20% of the protein (middle region), is shown in SEQ ID NO:6. The sequence of a portion of the cDNA insert from clone s12.pk127.m2 is shown in SEQ ID NO:7; the deduced amino acid sequence of this cDNA, which represents 26% of the protein (middle region) is shown in SEQ ID NO:8. The sequence of a portion of the cDNA insert from clone wre1n.pk0059.e1 is shown in SEQ ID NO:9; the deduced amino acid sequence of this cDNA, which represents 12% of the protein (middle region) is shown in SEQ ID NO:10.

BLAST scores and probabilities indicate that the instant nucleic acid fragments encode portions of BCS1 proteins. These sequences represent the first corn, rice, soybean and wheat sequences encoding BCS1 proteins.

Example 4

Characterization of cDNA Clones Encoding 6-Phosphofructo 2-Kinase/Fructose 2,6-Bisphosphatase The BLASTX search using the EST sequence from clone cs1.pk0039.d2 revealed similarity of the protein encoded by the cDNA to 6-phosphofructo 2-kinase/fructose 2,6-bisphosphatase from *Spinacia oleracea* (NCBI Identifier No. gi 3170230). The BLASTX search using the EST sequences from clones fds.pk0026.a2, rls6.pk0007.b6, rds2c.pk005.d2, rlr6.pk0085.b4, rls48.pk0013.b4, src2c.pk003.p13, wlsu2.pk029.l11 and wkm2c.pk006.h13 revealed similarity of the proteins encoded by the cDNAs to 6-phosphofructo 2-kinase/fructose 2,6-bisphosphatase from *Solanum tuberosum* (NCBI Identifier No. gi 3309583).

In the process of comparing the ESTs it was found that rice clones rls6.pk0007.b6, rds2c.pk005.d2, rlr6.pk0085.b4 and rls48.pk0013.b4 had overlapping regions of homology. Wheat clones wlsu2.pk029.l11 and wkm2c.pk006.h13 were also found to have overlapping regions of homology. Using this homology it was possible to align the ESTs and assemble two contigs encoding a unique rice and wheat 6-phosphofructo 2-kinase/fructose 2,6-bisphosphatase proteins.

The BLAST results for each of these ESTs and the rice and wheat contigs are shown in Table 4:

TABLE 4

BLAST Results for Clones Encoding Polypeptides Homologous to *Spinacia oleracea* and *Solanum tuberosum* 6-Phosphofructo 2-Kinase/Fructose 2,6-Bisphosphatase Proteins

| Clone | BLAST pLog Score |
| --- | --- |
| cs1.pk0039.d2 | 82.00 |
| fds.pk0026.a2 | 58.10 |
| Contig composed of: | 151.00 |
| rls6.pk0007.b6 | |
| rds2c.pk005.d2 | |
| rlr6.pk0085.b4 | |
| rls48.pk0013.b4 | |
| src2c.pk003.p13 | 101.00 |
| Contig composed of: | 84.70 |
| wlsu2.pk029.l11 | |
| wkm2c.pk006.h13 | |

The sequence of a portion of the cDNA insert from clone cs1.pk0039.d2 is shown in SEQ ID NO:11; the deduced amino acid sequence of this cDNA, which represents 20% of the protein (middle region), is shown in SEQ ID NO:12. The sequence of a portion of the cDNA insert from clone fds.pk0026.a2 is shown in SEQ ID NO:13; the deduced amino acid sequence of this cDNA, which represents 32% of the protein (middle region), is shown in SEQ ID NO:14. The sequence of the rice contig composed of clones rls6.pk0007.b6, rds2c.pk005.d2, rlr6.pk0085.b4 and rls48.pk0013.b4 is shown in SEQ ID NO:15; the deduced amino acid sequence of this contig, which represents 50% of the protein (C-terminal region), is shown in SEQ ID NO:16. The sequence of a portion of the cDNA insert from clone src2c.pk003.p13 is shown in SEQ ID NO:17; the deduced amino acid sequence of this cDNA, which represents 36% of the protein (middle region), is shown in SEQ ID NO:18. The sequence of the wheat contig composed of clones wlsu2.pk029.l11 and wkm2c.pk006.h13 is shown in SEQ ID NO:19; the deduced amino acid sequence of this contig, which represents 28% of the protein (C-terminal region), is shown in SEQ ID NO:20.

BLAST scores and probabilities indicate that the instant nucleic acid fragments encode portions of 6-phosphofructo 2-kinase/fructose 2,6-bisphosphatase proteins. These sequences represent the first corn, Momordica, rice, soybean and wheat sequences encoding 6-phosphofructo 2-kinase/fructose 2,6-bisphosphatase.

Example 5

Expression of Chimeric Genes in Monocot Cells

A chimeric gene comprising a cDNA encoding a glycolysis or respiration protein in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110–2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf (+) (Promega). Vector and insert DNA can be ligated at 15° C. overnight, essentially as described (Maniatis). The ligated DNA may then be used to transform *E. coli* XL1-Blue (*Epicurian Coli* XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding a glycolysis or respiration protein, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al., (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al., (1987) *Nature* 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al., (1990) *Bio/Technology* 8:833–839).

Example 6

Expression of Chimeric Genes in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228–9238) can be used for expression of the instant glycolysis and respiration proteins in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embroys may then be transformed with the expression vector comprising a sequences encoding a glycolysis or respiration protein. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Kline et al. (1987) Nature (London) 327:70, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al.(1985) Nature 313:810–812), the hygromycin phosphotransferase gene from plasmid pJR225 (from E. coli; Gritz et al.(1983) Gene 25:179–188) and the 3' region of the nopaline synthase gene from the T-DNA of the Ti plasmid of Agrobacterium tumefaciens. The seed expression cassette comprising the phaseolin 5' region, the fragment encoding the glycolysis or respiration protein and the phaseolin 3' region can be isolated as a restriction fragment. This fragment can then be inserted into a unique restriction site of the vector carrying the marker gene.

To 50 µL of a 60 mg/mL 1 µm gold particle suspension is added (in order): 5 µL DNA (1 µg/µL), 20 µl spermidine (0.1 M), and 50 µL CaCl$_2$ (2.5 M). The particle preparation is then agitated for three minutes, spun in a microfuge for 10 seconds and the supernatant removed. The DNA-coated particles are then washed once in 400 µL 70% ethanol and resuspended in 40 µL of anhydrous ethanol. The DNA/particle suspension can be sonicated three times for one second each. Five µL of the DNA-coated gold particles are then loaded on each macro carrier disk.

Approximately 300–400 mg of a two-week-old suspension culture is placed in an empty 60x15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 7

Expression of Chimeric Genes in Microbial Cells

The cDNAs encoding the instant glycolysis and respiration proteins can be inserted into the T7 E. coli expression vector pBT430. This vector is a derivative of pET-3a (Rosenberg et al. (1987) Gene 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 µg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 µL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as decribed above. The prepared vector pBT430 and fragment can then be ligated at 16° C. for 15 hours followed by transformation into DH5 electrocompetent cells (GIBCO BRL). Transformants can be selected on agar plates containing LB media and 100 µg/mL ampicillin. Transformants containing the gene encoding the glycolysis or respiration protein are then screened for the correct orientation with respect to the T7 promoter by restriction enzyme analysis.

For high level expression, a plasmid clone with the cDNA insert in the correct orientation relative to the T7 promoter can be transformed into E. coli strain BL21(DE3) (Studier et al. (1986) J. Mol. Biol. 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 µL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One µg of protein from the soluble fraction of the culture can be separated by SDS-polyacrylamide gel electrophoresis. Gels can be observed for protein bands migrating at the expected molecular weight.

What is claimed is:

1. An isolated polynucleotide comprising:

(a) a first nucleotide sequence encoding a BCS1 polypeptide that is at least 62 amino acids in length and that has at least 80% identity based on the Clustal method of alignment when compared to a member selected from the group consisting of SEQ ID NOs:2, 4, 6, 8 and 10; or (b) a second nucleotide sequence that is a complement of the first nucleotide sequence.

2. The isolated polynucleotide of claim 1, wherein the first nucleotide sequence is selected from the group consisting of SEQ ID NOs:1, 3, 5, 7 and 9.

3. The isolated polynucleotide of claim 1 wherein the polynucleotide sequence is DNA.

4. The isolated polynucleotide of claim 1 wherein the polynucleotide is RNA.

5. A chimeric gene comprising the isolated polynucleotide of claim 1 operably linked to at least one suitable regulatory sequence.

6. An isolated host cell transformed with the chimeric gene of claim 5.

7. A host cell comprising an isolated polynucleotide of claim 1.

8. The host cell of claim 7 wherein the host cell is a bacterial cell or a plant cell.

9. A method for altering the expression level of a BCS1 gene in a host cell having an indigenous BCS1 gene, the method comprising:

(a) transforming a host cell with the chimeric gene of claim 5 to produce a transformed host cell; and (b) growing the transformed host cell under conditions that are suitable for the expression of the chimeric gene whereby the expression level of the indigenous BCS1 gene is altered.

* * * * *

SEQUENCE LISTING

<160> NUMBER OF SEQ ID NOS: 21

<210> SEQ ID NO 1
<211> LENGTH: 1478
<212> TYPE: DNA
<213> ORGANISM: Zea mays
<220> FEATURE:
<221> NAME/KEY: unsure
<222> LOCATION: (23)
<220> FEATURE:
<221> NAME/KEY: unsure
<222> LOCATION: (40)
<220> FEATURE:
<221> NAME/KEY: unsure
<222> LOCATION: (44)
<220> FEATURE:
<221> NAME/KEY: unsure
<222> LOCATION: (92)
<220> FEATURE:
<221> NAME/KEY: unsure
<222> LOCATION: (111)
<220> FEATURE:
<221> NAME/KEY: unsure
<222> LOCATION: (137)
<220> FEATURE:
<221> NAME/KEY: unsure
<222> LOCATION: (152)..(153)
<220> FEATURE:
<221> NAME/KEY: unsure
<222> LOCATION: (162)
<220> FEATURE:
<221> NAME/KEY: unsure
<222> LOCATION: (182)
<220> FEATURE:
<221> NAME/KEY: unsure
<222> LOCATION: (207)
<220> FEATURE:
<221> NAME/KEY: unsure
<222> LOCATION: (285)
<220> FEATURE:
<221> NAME/KEY: unsure
<222> LOCATION: (306)
<220> FEATURE:
<221> NAME/KEY: unsure
<222> LOCATION: (382)
<220> FEATURE:
<221> NAME/KEY: unsure
<222> LOCATION: (386)
<220> FEATURE:
<221> NAME/KEY: unsure
<222> LOCATION: (398)
<220> FEATURE:
<221> NAME/KEY: unsure
<222> LOCATION: (409)
<220> FEATURE:
<221> NAME/KEY: unsure
<222> LOCATION: (819)
<220> FEATURE:
<221> NAME/KEY: unsure
<222> LOCATION: (1191)
<220> FEATURE:
<221> NAME/KEY: unsure
<222> LOCATION: (1316)
<220> FEATURE:
<221> NAME/KEY: unsure
<222> LOCATION: (1331)
<220> FEATURE:
<221> NAME/KEY: unsure
<222> LOCATION: (1376)
<220> FEATURE:
<221> NAME/KEY: unsure
<222> LOCATION: (1395)
<220> FEATURE:
<221> NAME/KEY: unsure
<222> LOCATION: (1415)
<220> FEATURE:

<221> NAME/KEY: unsure
<222> LOCATION: (1472)..(1473)

<400> SEQUENCE: 1

| | | | | | |
|---|---|---|---|---|---|
| agaatcagcc | tcggtcacgg | ttnaggggca | gacctattn | gctngagagg | cgggagatgc | 60 |
| cgagtgaccc | gcgccgatta | agtgcgcctg | tntccggacg | gaccggaacg | ntggcaacgc | 120 |
| ggcggcaacg | gccacgncaa | cggccacgcc | cnnggcggca | gntacgggtc | gaggtccgct | 180 |
| cnttcgagat | gagcttccac | aggcggnaaa | ggagaaggcc | atcggtccta | cctcccggac | 240 |
| atcctctccg | aggccaagaa | gatcaaggac | caggaccgga | cgctnaagat | ctacatgaac | 300 |
| gagggngagt | cctggttcgc | catcgacctc | caccacccgt | ccaccttcac | cacgctcgcc | 360 |
| atggaccgca | agatgaagcg | gnccgnaatg | gacgaccncg | asaggttcnt | caggaggaaa | 420 |
| gattactaca | ggaagattgg | caaggcatgg | aagcggggtt | accttctgta | tggtccacct | 480 |
| gggactggga | agtcaagcct | aatcgcagcc | atggccaacc | atctcaggtt | tgacatatat | 540 |
| gatctcgagc | taactgcggt | cacatccaac | tcagacctca | ggaggcttct | tgttaacatg | 600 |
| gacaaccgat | ccattctagt | cattgaagat | attgactgca | ccatcgaact | caaacaacgg | 660 |
| caggaggccg | aggacatga | tgagtcagat | tctacagaac | aaaacaaggg | ggaaggcaag | 720 |
| gtaacgctgt | ctggactgct | caactttgtt | gatgggctgt | ggtcaacaag | tggggaagaa | 780 |
| ggatcatcgt | cttcaacaac | caattacaag | gagcggctng | acccggcact | gctgcggcct | 840 |
| ggaaggatgg | acatgcacat | ccacatgggg | tattgcaccc | cagagtcttt | ccaaatcctt | 900 |
| gccaacaact | accactccat | cgagtaccat | gacacgtatc | cagagattga | gaaactgatc | 960 |
| aaggaggtga | cggttacgcc | cgcagaggtt | gctgaggttc | tgatgaggaa | cgatgacact | 1020 |
| gatgttgtgc | tccatgatct | tgtcgatttc | ctgaagtcaa | aaatcaagga | tgccaatgag | 1080 |
| atcaagactg | aacacaagga | aagcagacaa | ccagctagat | gagaagaaaa | atgcaaaaa | 1140 |
| ataaaccca | gtgcatttct | tccaaaaaag | aagatgaaag | ctaatggcgg | nttaagactg | 1200 |
| agcacaagga | acaaataacc | agctggatga | agagaaaggc | aaccagatag | tgagaaaaaa | 1260 |
| aaacagggca | aattccttt | aagagaagga | aaggaagatg | aaagcaaccc | aatcgnattt | 1320 |
| catattggat | nggatcctac | agggatcca | ttggcatatg | ggaatggttt | ggatantggt | 1380 |
| aacattatgg | ttttngggaa | caatggaggg | gtaanggac | cttgaaggga | ttttggaaaa | 1440 |
| atttgtaagg | cttggttaag | aaccttgttt | cnnaactt | | | 1478 |

<210> SEQ ID NO 2
<211> LENGTH: 226
<212> TYPE: PRT
<213> ORGANISM: Zea mays
<220> FEATURE:
<221> NAME/KEY: UNSURE
<222> LOCATION: (49)..(50)
<220> FEATURE:
<221> NAME/KEY: UNSURE
<222> LOCATION: (54)..(55)
<220> FEATURE:
<221> NAME/KEY: UNSURE
<222> LOCATION: (58)

<400> SEQUENCE: 2

Asp Ile Leu Ser Glu Ala Lys Lys Ile Lys Asp Gln Asp Arg Thr Leu
1               5                   10                  15

Lys Ile Tyr Met Asn Glu Gly Glu Ser Trp Phe Ala Ile Asp Leu His
            20                  25                  30

```
His Pro Ser Thr Phe Thr Thr Leu Ala Met Asp Arg Lys Met Lys Arg
             35                  40                  45

Xaa Xaa Met Asp Asp Xaa Xaa Arg Phe Xaa Arg Arg Lys Asp Tyr Tyr
 50                  55                  60

Arg Lys Ile Gly Lys Ala Trp Lys Arg Gly Tyr Leu Leu Tyr Gly Pro
 65                  70                  75                  80

Pro Gly Thr Gly Lys Ser Ser Leu Ile Ala Ala Met Ala Asn His Leu
                 85                  90                  95

Arg Phe Asp Ile Tyr Asp Leu Glu Leu Thr Ala Val Thr Ser Asn Ser
                100                 105                 110

Asp Leu Arg Arg Leu Leu Val Asn Met Asp Asn Arg Ser Ile Leu Val
                115                 120                 125

Ile Glu Asp Ile Asp Cys Thr Ile Glu Leu Lys Gln Arg Gln Glu Ala
            130                 135                 140

Glu Gly His Asp Glu Ser Asp Ser Thr Glu Gln Asn Lys Gly Glu Gly
145                 150                 155                 160

Lys Val Thr Leu Ser Gly Leu Leu Asn Phe Val Asp Gly Leu Trp Ser
                165                 170                 175

Thr Ser Gly Glu Glu Gly Ser Ser Ser Ser Thr Thr Asn Tyr Lys Glu
                180                 185                 190

Arg Leu Asp Pro Ala Leu Leu Arg Pro Gly Arg Met Asp Met His Ile
            195                 200                 205

His Met Gly Tyr Cys Thr Pro Glu Ser Phe Gln Ile Leu Ala Asn Asn
        210                 215                 220

Tyr His
225

<210> SEQ ID NO 3
<211> LENGTH: 945
<212> TYPE: DNA
<213> ORGANISM: Oryza sativa

<400> SEQUENCE: 3
gcacgaggca acgccgagcg ccgcagctac cgcctcacct tccaccgccg ccaccgcgcg      60
ctcgtcgaga acgcctacct tccccacgtc ctcgccgagg gccgcgccgt caccgtccgc     120
aaccgccagc gccgcctctt caccaacaac cccagcgccg actggtctgc ctacgacgac     180
gcccgcgtct ggagccacgt caagctggag caccccctcca ccttcgccac gctcgccatg     240
gaccccgtcc ggaagcagga gatcatcgac gacctcgaca tgttccgcga cggcaaggaa     300
tactacgcct ccgtcggcaa ggcgtggaaa cgcggctacc tgctgttcgg gccacccggc     360
acaggcaagt ccaccatgat cgccgccatg gcaaacttcc tagactacgg cgtctacgac     420
ctcgagctga cggcagtcaa gagcaacacc gagctacgga ggctgttcat cgagaccacc     480
ggaaagtcga tcatcgtcat cgaggacatc gactgctcca tcgacctcac cggcaagcgc     540
aagaagaaga aaaaggacaa gaagaagaag aagatgacgc caccttgggc ccgcgacgat     600
gacgaggagc ttatgtggag agagatgta acaaaaagtt aaaggtgttg gttctcatgc      660
aagagctagc ttaacacaag ctccaagaca aatacaatta atgtataggt gagagataga     720
gagaggagaa gaaaattgta gtcaacctta tagctaatct attatatgtg ttggcttttaa    780
gattagctaa tagtaggaag tgagctctat tattatcctt gctctaagat atgacaatag     840
aaactacact ctacaaccca tgatttctta agtgggccct taataaata catcattcct      900
cttctctacc aatcaaaaaa aaaaaaaaaa aaaaaaaaaa aaaaa                     945
```

```
<210> SEQ ID NO 4
<211> LENGTH: 213
<212> TYPE: PRT
<213> ORGANISM: Oryza sativa

<400> SEQUENCE: 4

Ala Arg Gly Asn Ala Glu Arg Arg Ser Tyr Arg Leu Thr Phe His Arg
 1               5                  10                  15

Arg His Arg Ala Leu Val Glu Asn Ala Tyr Leu Pro His Val Leu Ala
            20                  25                  30

Glu Gly Arg Ala Val Thr Val Arg Asn Arg Gln Arg Leu Phe Thr
        35                  40                  45

Asn Asn Pro Ser Ala Asp Trp Ser Ala Tyr Asp Ala Arg Val Trp
 50                  55                  60

Ser His Val Lys Leu Glu His Pro Ser Thr Phe Ala Thr Leu Ala Met
 65                  70                  75                  80

Asp Pro Val Arg Lys Gln Glu Ile Ile Asp Leu Asp Met Phe Arg
                85                  90                  95

Asp Gly Lys Glu Tyr Tyr Ala Ser Val Gly Lys Ala Trp Lys Arg Gly
            100                 105                 110

Tyr Leu Leu Phe Gly Pro Pro Gly Thr Gly Lys Ser Thr Met Ile Ala
            115                 120                 125

Ala Met Ala Asn Phe Leu Asp Tyr Gly Val Tyr Asp Leu Glu Leu Thr
130                 135                 140

Ala Val Lys Ser Asn Thr Glu Leu Arg Arg Leu Phe Ile Glu Thr Thr
145                 150                 155                 160

Gly Lys Ser Ile Ile Val Ile Glu Asp Ile Asp Cys Ser Ile Asp Leu
                165                 170                 175

Thr Gly Lys Arg Lys Lys Lys Lys Asp Lys Lys Lys Lys Met
            180                 185                 190

Thr Pro Pro Trp Ala Arg Asp Asp Glu Glu Leu Met Trp Arg Arg
            195                 200                 205

Asp Val Thr Lys Ser
        210

<210> SEQ ID NO 5
<211> LENGTH: 547
<212> TYPE: DNA
<213> ORGANISM: Oryza sativa
<220> FEATURE:
<221> NAME/KEY: unsure
<222> LOCATION: (486)
<220> FEATURE:
<221> NAME/KEY: unsure
<222> LOCATION: (515)
<220> FEATURE:
<221> NAME/KEY: unsure
<222> LOCATION: (528)
<220> FEATURE:
<221> NAME/KEY: unsure
<222> LOCATION: (530)

<400> SEQUENCE: 5
cggcgtcatc cggcggtggc gcgagctaac cgccaaggac cggcagaggc tgctgttcac      60
caaccactcc aggcaagggg agagcatgtg gaccagtgtc ccgtacaatc ccccggcgac     120
attcgacatg ctcgccatgg accatgccaa gaaggttgag atcatggacg atctcagggc     180
attccagaag ggaaaggaat accactccaa ggtcggcaag ccatggaagc ggggctacct     240
tctgcacggg ccaccgggca cgggtaagac caccatgatc gggtctatgg ccaacttcct     300
```

-continued

```
cgactatgac gtatacgacc tcgaccttac atcgatcaag acaacgccg agctgcggaa        360 ctcttccttg acacgacaga caaatccatc atcgttatcg aggacatcga cgcatcgagg       420
tcgactacta caagcgtaag ggcataagat gacaacgcga ggaagtgaca acaccattgg       480
tgtcancttt caacaagctg tataaagcaa gtacntgtcg gctgctancn tctcgtggcg       540
tgtcgct                                                                 547
```

<210> SEQ ID NO 6
<211> LENGTH: 65
<212> TYPE: PRT
<213> ORGANISM: Oryza sativa

<400> SEQUENCE: 6

Met Asp His Ala Lys Lys Val Glu Ile Met Asp Asp Leu Arg Ala Phe
1               5                   10                  15

Gln Lys Gly Lys Glu Tyr His Ser Lys Val Gly Lys Pro Trp Lys Arg
            20                  25                  30

Gly Tyr Leu Leu His Gly Pro Pro Gly Thr Gly Lys Thr Thr Met Ile
        35                  40                  45

Gly Ser Met Ala Asn Phe Leu Asp Tyr Asp Val Tyr Asp Leu Asp Leu
    50                  55                  60

Thr
65

<210> SEQ ID NO 7
<211> LENGTH: 513
<212> TYPE: DNA
<213> ORGANISM: Glycine max
<220> FEATURE:
<221> NAME/KEY: unsure
<222> LOCATION: (442)

<400> SEQUENCE: 7

```
agcttgattg ctgccatggc gaattacttg aagtttgatg tgtatgattt ggagctgacg        60
gagctgaatg ctaactcgga gctcaggagg ttgctcattg caatggcgaa taggtccatt       120
cttgttgtgg aggacattga ttgcactgtt gagtttcatg atcggagagc tgaggccaga       180
gctgcttctg gacataacaa cgacagacag gttacactat cgggtttgct taatttcatt       240
gatgggttat ggtcaagttg tggggatgag aggatcatag tgttcacaac aaaccacaag       300
gacaagcttg accctgcatt gctgcgccct ggtcgaatgg atgttcacat tcacatgtcc       360
tattgcactc cctgtggttt caggcagcta gcttccaatt acctcggaat caaaagagca       420
ttctctcttc gaaaagatcg angaagagat gcaagaaaac caagtgactc ctgctgaagg       480
taacaagaac agcttctgaa gagcaaccac atc                                    513
```

<210> SEQ ID NO 8
<211> LENGTH: 136
<212> TYPE: PRT
<213> ORGANISM: Glycine max

<400> SEQUENCE: 8

Ser Leu Ile Ala Ala Met Ala Asn Tyr Leu Lys Phe Asp Val Tyr Asp
1               5                   10                  15

Leu Glu Leu Thr Glu Leu Asn Ala Asn Ser Glu Leu Arg Arg Leu Leu
            20                  25                  30

Ile Ala Met Ala Asn Arg Ser Ile Leu Val Val Glu Asp Ile Asp Cys
        35                  40                  45

```
Thr Val Glu Phe His Asp Arg Arg Ala Glu Ala Arg Ala Ala Ser Gly
        50                  55                  60

His Asn Asn Asp Arg Gln Val Thr Leu Ser Gly Leu Leu Asn Phe Ile
 65                  70                  75                  80

Asp Gly Leu Trp Ser Ser Cys Gly Asp Glu Arg Ile Ile Val Phe Thr
                 85                  90                  95

Thr Asn His Lys Asp Lys Leu Asp Pro Ala Leu Leu Arg Pro Gly Arg
                100                 105                 110

Met Asp Val His Ile His Met Ser Tyr Cys Thr Pro Cys Gly Phe Arg
            115                 120                 125

Gln Leu Ala Ser Asn Tyr Leu Gly
    130                 135

<210> SEQ ID NO 9
<211> LENGTH: 602
<212> TYPE: DNA
<213> ORGANISM: Triticum aestivum
<220> FEATURE:
<221> NAME/KEY: unsure
<222> LOCATION: (422)
<220> FEATURE:
<221> NAME/KEY: unsure
<222> LOCATION: (449)
<220> FEATURE:
<221> NAME/KEY: unsure
<222> LOCATION: (462)
<220> FEATURE:
<221> NAME/KEY: unsure
<222> LOCATION: (567)
<220> FEATURE:
<221> NAME/KEY: unsure
<222> LOCATION: (588)
<220> FEATURE:
<221> NAME/KEY: unsure
<222> LOCATION: (595)

<400> SEQUENCE: 9
cgagggccgc gccgtcaccg tcaagaaccg ccagcgccgt ctcttcacca acaacgccag      60
ccgcaactgg aacccctacc gcagcaagag cgtctggagc cacgtccct tcgaacaccc     120 cgccaccttc gacacgcttg ccatgcaccc cgatgagaag gaggccatcg ttgacgacct     180
catggcgttc caggagagca aggactacta tgccaaggtc ggcaaggcgt ggaagcgcgg     240
gtacctcctt tatggaccgc ccggcaccgg caagtccacc atgatcgccg ccatggccaa     300
cttccttgac tacgacgtct acgatctcga ggtcgacggt atcgataact tgatatcgaa     360
tcggcacgat gaaggaggac gacagcaact ggccggaccc gacgcgtcgg caggaagact     420
cnagatgtca tgggaacgac aatctcctna cactccaag tnggtcctcg ttgactcaga      480
caacaaggac cggaggctcc gcatctctac aactgtcaag acttaaattt ctgtttacta     540
taactcactt agatagctat tactttngca agttggtttc cgtggtanga cgcangtaaa     600
at                                                                   602

<210> SEQ ID NO 10
<211> LENGTH: 62
<212> TYPE: PRT
<213> ORGANISM: Triticum aestivum

<400> SEQUENCE: 10

Thr Leu Ala Met His Pro Asp Glu Lys Glu Ala Ile Val Asp Asp Leu
  1               5                  10                  15
```

```
Met Ala Phe Gln Glu Ser Lys Asp Tyr Tyr Ala Lys Val Gly Lys Ala
            20                  25                  30

Trp Lys Arg Gly Tyr Leu Leu Tyr Gly Pro Pro Gly Thr Gly Lys Ser
            35                  40                  45

Thr Met Ile Ala Ala Met Ala Asn Phe Leu Asp Tyr Asp Val
            50                  55                  60

<210> SEQ ID NO 11
<211> LENGTH: 464
<212> TYPE: DNA
<213> ORGANISM: Zea mays

<400> SEQUENCE: 11
gcacgaggtt gcagctgcag ctgtagctga tcgtttgcat gggtcaaagg aggaccggaa      60
gctggccatt gttttggttg gcctaccagc tcgtggtaaa accttcactg cagttaagct     120
tacaaggtac cttcgttggt tgggccatga aactagacat ttcaatgttg ggaagtatcg     180
ccgtcttaag cttggagcaa atcagtctgc agatttttc cgtgatgata atcctgaagg      240
tattgaggca cgtaatgagg tggctgcttt agcaatggag gacatgatag attggatgaa     300
tggtggaggt caggttggta tatttgacgc aacaaacagc acaagaaagc gaagatatat     360
gctaatgaaa atggctgaag gtaactgtaa gattatattt ttggagacaa tatgtaatga     420
tccaaacata attgaaagaa acatacgggt gaagattcaa caag                      464

<210> SEQ ID NO 12
<211> LENGTH: 152
<212> TYPE: PRT
<213> ORGANISM: Zea mays

<400> SEQUENCE: 12

Val Ala Ala Ala Val Ala Asp Arg Leu His Gly Ser Lys Glu Asp
1               5                   10                  15

Arg Lys Leu Ala Ile Val Leu Val Gly Leu Pro Ala Arg Gly Lys Thr
            20                  25                  30

Phe Thr Ala Val Lys Leu Thr Arg Tyr Leu Arg Trp Leu Gly His Glu
            35                  40                  45

Thr Arg His Phe Asn Val Gly Lys Tyr Arg Arg Leu Lys Leu Gly Ala
            50                  55                  60

Asn Gln Ser Ala Asp Phe Phe Arg Asp Asp Asn Pro Glu Gly Ile Glu
65                  70                  75                  80

Ala Arg Asn Glu Val Ala Ala Leu Ala Met Glu Asp Met Ile Asp Trp
                85                  90                  95

Met Asn Gly Gly Gly Gln Val Gly Ile Phe Asp Ala Thr Asn Ser Thr
            100                 105                 110

Arg Lys Arg Arg Tyr Met Leu Met Lys Met Ala Glu Gly Asn Cys Lys
            115                 120                 125

Ile Ile Phe Leu Glu Thr Ile Cys Asn Asp Pro Asn Ile Ile Glu Arg
            130                 135                 140

Asn Ile Arg Val Lys Ile Gln Gln
145                 150

<210> SEQ ID NO 13
<211> LENGTH: 594
<212> TYPE: DNA
<213> ORGANISM: Momordica charantia
<220> FEATURE:
<221> NAME/KEY: unsure
<222> LOCATION: (308)
```

```
<220> FEATURE:
<221> NAME/KEY: unsure
<222> LOCATION: (457)
<220> FEATURE:
<221> NAME/KEY: unsure
<222> LOCATION: (472)
<220> FEATURE:
<221> NAME/KEY: unsure
<222> LOCATION: (542)
<220> FEATURE:
<221> NAME/KEY: unsure
<222> LOCATION: (575)..(576)..(577)
<220> FEATURE:
<221> NAME/KEY: unsure
<222> LOCATION: (586)

<400> SEQUENCE: 13
gagacaaagc atttcaacgt tggcaagtac cgacgcctaa agcatggtgc taatcagtct      60
gcagactttt ttcgagctga caatccagaa ggcatggagg cacgtaatga gctgctctag     120
ctatggagga tatgatttct ggatgcagg aaggtggcca ggttggaata tttgatgcca     180
caaacagtac caggaaacgg agaaacatgt tgatgaaatt ggctgaagga aatattatt    240 tttctgggaa acctatgcaa tgatgaacgc atcattgaaa ggaatatacg tcttaaaata    300
caacaaancc tgattatgca gaggagccgg ttttgagct ggttgtccgt gacttcaaag    360
tcgcctaaga caactatgaa aaagttatga actgttgaag agggtcctac attaaaatga    420
ttgatatggt tagtggcatg gaggacaaaa caagtancaa cacagtgggt ancactggac    480
gattgccttt ctgggaata ccattaaaca agccaatatg ccactagcat gaaatatggt    540
anttaaggag atgggggccg gattaacagg cgggnnnatc aaaacngcaa cttt          594

<210> SEQ ID NO 14
<211> LENGTH: 149
<212> TYPE: PRT
<213> ORGANISM: Momordica charantia
<220> FEATURE:
<221> NAME/KEY: UNSURE
<222> LOCATION: (38)
<220> FEATURE:
<221> NAME/KEY: UNSURE
<222> LOCATION: (80)
<220> FEATURE:
<221> NAME/KEY: UNSURE
<222> LOCATION: (106)
<220> FEATURE:
<221> NAME/KEY: UNSURE
<222> LOCATION: (126)
<220> FEATURE:
<221> NAME/KEY: UNSURE
<222> LOCATION: (136)

<400> SEQUENCE: 14

Glu Thr Lys His Phe Asn Val Gly Lys Tyr Arg Arg Leu Lys His Gly
1               5                  10                  15

Ala Asn Gln Ser Ala Asp Phe Phe Arg Ala Asp Asn Pro Glu Gly Met
            20                  25                  30

Glu Ala Arg Asn Glu Xaa Ala Ala Leu Ala Met Glu Asp Met Ile Ser
        35                  40                  45

Trp Met Gln Glu Gly Gly Gln Val Gly Ile Phe Asp Ala Thr Asn Ser
    50                  55                  60

Thr Arg Lys Arg Arg Asn Met Leu Met Lys Leu Ala Glu Gly Lys Xaa
65                  70                  75                  80

Asn Ile Ile Phe Leu Gly Asn Leu Cys Asn Asp Glu Arg Ile Ile Glu
                85                  90                  95
```

Arg Asn Ile Arg Leu Lys Ile Gln Gln Xaa Pro Asp Tyr Ala Glu Glu
                100                 105                 110

Pro Val Phe Glu Leu Val Val Arg Asp Phe Lys Val Ala Xaa Asp Asn
        115                 120                 125

Tyr Glu Lys Val Met Asn Cys Xaa Arg Gly Ser Tyr Ile Lys Met Ile
    130                 135                 140

Asp Met Val Ser Gly
145

<210> SEQ ID NO 15
<211> LENGTH: 857
<212> TYPE: DNA
<213> ORGANISM: Oryza sativa
<220> FEATURE:
<221> NAME/KEY: unsure
<222> LOCATION: (11)
<220> FEATURE:
<221> NAME/KEY: unsure
<222> LOCATION: (115)
<220> FEATURE:
<221> NAME/KEY: unsure
<222> LOCATION: (744)
<220> FEATURE:
<221> NAME/KEY: unsure
<222> LOCATION: (767)
<220> FEATURE:
<221> NAME/KEY: unsure
<222> LOCATION: (794)..(795)
<220> FEATURE:
<221> NAME/KEY: unsure
<222> LOCATION: (806)

<400> SEQUENCE: 15
gggaactgta ngattatatt tctggaaact atctgtaacg atccgaatat aattgaaagg      60
aatgtacgtc tgaagataca gcaaagtcct gactatgctg accagccaga ttatnaacct    120
ggagtgcggg acttcaagga acgcctggca aactatgaaa aggtgtatga gccagtgcag    180
gaaggttctt acattaaaat gattgatatg gtaaaagggc agggaggcca gttacaggtc    240
aacaatatca gtggttatct ccctggaagg attgtctttt tcttggtgaa ctctcatctt    300
acacctcgac ctattttgct tacaaggcat ggtgagagtt tacacaatgt cagaggaaga    360
gttggtggtg acacggtcct gagtgaagat ggagagcttt actcgaagaa attagccaac    420
ttcatagaaa agaggctcaa atctgagaaa actgcatcta tatggaccag cacgcttcag    480
aggacaattt tgacagcaag tccaatagtt ggattcccaa agatacaatg gcgtgctctt    540
gatgagataa actctggggt gtgtgatggg atgacgtatg aagagataaa gaaagttatg    600
cccgaggaat tgaatcacg caagaaggac aaattaagat atcgataccc ccgtggagaa    660
tcctaccttg atgtgattca gagactggaa cctgttatca ttgagctaga acgccagcga    720
gcaccagtag tcgttatttc ccancaggct gtattcgggc ctatatnata tttcgtgaca    780
ggctctgagg gaannccaga tattgngatg ctctccacac cataattgag tacaaatggg    840
agcacaggtg ttgagga                                                   857

<210> SEQ ID NO 16
<211> LENGTH: 251
<212> TYPE: PRT
<213> ORGANISM: Oryza sativa
<220> FEATURE:
<221> NAME/KEY: UNSURE
<222> LOCATION: (4)
<220> FEATURE:
<221> NAME/KEY: UNSURE
<222> LOCATION: (39)

```
<220> FEATURE:
<221> NAME/KEY: UNSURE
<222> LOCATION: (248)

<400> SEQUENCE: 16

Gly Asn Cys Xaa Ile Ile Phe Leu Glu Thr Ile Cys Asn Asp Pro Asn
1               5                   10                  15

Ile Ile Glu Arg Asn Val Arg Leu Lys Ile Gln Gln Ser Pro Asp Tyr
            20                  25                  30

Ala Asp Gln Pro Asp Tyr Xaa Pro Gly Val Arg Asp Phe Lys Glu Arg
        35                  40                  45

Leu Ala Asn Tyr Glu Lys Val Tyr Glu Pro Val Gln Glu Gly Ser Tyr
    50                  55                  60

Ile Lys Met Ile Asp Met Val Lys Gly Gln Gly Gln Leu Gln Val
65                  70                  75                  80

Asn Asn Ile Ser Gly Tyr Leu Pro Gly Arg Ile Val Phe Phe Leu Val
                85                  90                  95

Asn Ser His Leu Thr Pro Arg Pro Ile Leu Leu Thr Arg His Gly Glu
            100                 105                 110

Ser Leu His Asn Val Arg Gly Arg Val Gly Gly Asp Thr Val Leu Ser
        115                 120                 125

Glu Asp Gly Glu Leu Tyr Ser Lys Lys Leu Ala Asn Phe Ile Glu Lys
    130                 135                 140

Arg Leu Lys Ser Glu Lys Thr Ala Ser Ile Trp Thr Ser Thr Leu Gln
145                 150                 155                 160

Arg Thr Ile Leu Thr Ala Ser Pro Ile Val Gly Phe Pro Lys Ile Gln
                165                 170                 175

Trp Arg Ala Leu Asp Glu Ile Asn Ser Gly Val Cys Asp Gly Met Thr
            180                 185                 190

Tyr Glu Glu Ile Lys Lys Val Met Pro Glu Glu Phe Glu Ser Arg Lys
        195                 200                 205

Lys Asp Lys Leu Arg Tyr Arg Tyr Pro Arg Gly Glu Ser Tyr Leu Asp
    210                 215                 220

Val Ile Gln Arg Leu Glu Pro Val Ile Ile Glu Leu Glu Arg Gln Arg
225                 230                 235                 240

Ala Pro Val Val Val Ile Ser Xaa Gln Ala Val
                245                 250

<210> SEQ ID NO 17
<211> LENGTH: 546
<212> TYPE: DNA
<213> ORGANISM: Glycine max
<220> FEATURE:
<221> NAME/KEY: unsure
<222> LOCATION: (460)

<400> SEQUENCE: 17
ctgctgattt ctttcgagct gacaatcctg aaggtgtgga ggcacgtaat gaggtagcaa      60
agatggcatt tgaagatatg atatcttgga tgcaagaagg tggccaggtt gggatatttg     120
atgccacaaa cagtagcaag cagcgaagaa acatgctgat gaaattggct gaaggtagat     180
gcaagatcat tttctggaa acgatatgca atgatgttga cataattgag aggaatatac      240
gctttaaaat tcagcagagt cccgactatg cagaagtatc agattttgag gctgggttgc     300
gagactttaa agaacgtgtc gccaattatg agaaggttta tgagaccgta gaagaaggat     360
cttacataaa aatgattgac atggccagtg acatggagg gcaaatacaa gtgaaaaata     420
```

```
tcagtggcta cctacctggc cggatagtat gtttcctggn taatacacat cttacaccac    480
gcccaatatt acttacccgg catggagaaa gtcagtataa tgtgagaagc aaaattggtg    540
gagacc                                                               546
```

```
<210> SEQ ID NO 18
<211> LENGTH: 181
<212> TYPE: PRT
<213> ORGANISM: Glycine max
<220> FEATURE:
<221> NAME/KEY: UNSURE
<222> LOCATION: (153)

<400> SEQUENCE: 18
```

| Ala | Asp | Phe | Phe | Arg | Ala | Asp | Asn | Pro | Glu | Gly | Val | Glu | Ala | Arg | Asn |
|---|---|---|---|---|---|---|---|---|---|---|---|---|---|---|---|
| 1 | | | | 5 | | | | | 10 | | | | | 15 | |

| Glu | Val | Ala | Lys | Met | Ala | Phe | Glu | Asp | Met | Ile | Ser | Trp | Met | Gln | Glu |
|---|---|---|---|---|---|---|---|---|---|---|---|---|---|---|---|
| | | | 20 | | | | | 25 | | | | | 30 | | |

| Gly | Gly | Gln | Val | Gly | Ile | Phe | Asp | Ala | Thr | Asn | Ser | Ser | Lys | Gln | Arg |
|---|---|---|---|---|---|---|---|---|---|---|---|---|---|---|---|
| | | 35 | | | | | 40 | | | | | 45 | | | |

| Arg | Asn | Met | Leu | Met | Lys | Leu | Ala | Glu | Gly | Arg | Cys | Lys | Ile | Ile | Phe |
|---|---|---|---|---|---|---|---|---|---|---|---|---|---|---|---|
| | 50 | | | | | 55 | | | | | 60 | | | | |

| Leu | Glu | Thr | Ile | Cys | Asn | Asp | Val | Asp | Ile | Ile | Glu | Arg | Asn | Ile | Arg |
|---|---|---|---|---|---|---|---|---|---|---|---|---|---|---|---|
| 65 | | | | | 70 | | | | | 75 | | | | | 80 |

| Phe | Lys | Ile | Gln | Gln | Ser | Pro | Asp | Tyr | Ala | Glu | Val | Ser | Asp | Phe | Glu |
|---|---|---|---|---|---|---|---|---|---|---|---|---|---|---|---|
| | | | | 85 | | | | | 90 | | | | | 95 | |

| Ala | Gly | Leu | Arg | Asp | Phe | Lys | Glu | Arg | Val | Ala | Asn | Tyr | Glu | Lys | Val |
|---|---|---|---|---|---|---|---|---|---|---|---|---|---|---|---|
| | | | 100 | | | | | 105 | | | | | 110 | | |

| Tyr | Glu | Thr | Val | Glu | Glu | Gly | Ser | Tyr | Ile | Lys | Met | Ile | Asp | Met | Ala |
|---|---|---|---|---|---|---|---|---|---|---|---|---|---|---|---|
| | | 115 | | | | | 120 | | | | | 125 | | | |

| Ser | Gly | His | Gly | Gly | Gln | Ile | Gln | Val | Lys | Asn | Ile | Ser | Gly | Tyr | Leu |
|---|---|---|---|---|---|---|---|---|---|---|---|---|---|---|---|
| | 130 | | | | | 135 | | | | | 140 | | | | |

| Pro | Gly | Arg | Ile | Val | Cys | Phe | Leu | Xaa | Asn | Thr | His | Leu | Thr | Pro | Arg |
|---|---|---|---|---|---|---|---|---|---|---|---|---|---|---|---|
| 145 | | | | | 150 | | | | | 155 | | | | | 160 |

| Pro | Ile | Leu | Leu | Thr | Arg | His | Gly | Glu | Ser | Gln | Tyr | Asn | Val | Arg | Ser |
|---|---|---|---|---|---|---|---|---|---|---|---|---|---|---|---|
| | | | | 165 | | | | | 170 | | | | | 175 | |

| Lys | Ile | Gly | Gly | Asp |
|---|---|---|---|---|
| | | | 180 | |

```
<210> SEQ ID NO 19
<211> LENGTH: 736
<212> TYPE: DNA
<213> ORGANISM: Triticum aestivum
<220> FEATURE:
<221> NAME/KEY: unsure
<222> LOCATION: (625)
<220> FEATURE:
<221> NAME/KEY: unsure
<222> LOCATION: (631)
<220> FEATURE:
<221> NAME/KEY: unsure
<222> LOCATION: (657)
<220> FEATURE:
<221> NAME/KEY: unsure
<222> LOCATION: (662)
<220> FEATURE:
<221> NAME/KEY: unsure
<222> LOCATION: (688)
<220> FEATURE:
<221> NAME/KEY: unsure
<222> LOCATION: (691)
<220> FEATURE:
<221> NAME/KEY: unsure
<222> LOCATION: (713)
```

<220> FEATURE:
<221> NAME/KEY: unsure
<222> LOCATION: (734)

<400> SEQUENCE: 19

```
ccgaggtgga ctagcactct acagagaaca attttgacag caactccaat tgttggattc      60
ccaaagatac aatggcgtgc tcttgatgag atcaattctg gtgtatgtga tgggatgacg     120
tatgaagaga taaagaaaat tatgcctgag gaatatgagt cacgcaagaa ggacaagctg     180
cgttatcggt acccgcgtgg ggagtcttac cttgacgtga ttcagaggtt ggagcctgtt     240
atcatcgagc tcgaacgcca gcgagcacca gtggtcgtta tcccacca ggccgtattg      300
cgagcgctgt actcgtattt tgccgacagg cctttgaggg aagttccaga catggagatg     360
ccactccata ccataatcga gatacaaatg ggcgtcaccg gtgtcgagga aagaggtac     420
aagctcatgg attgagaatc tgagatacag gtaggctcag cacaacagca agttccggac     480
tggctgctcc agatacaacc atacagacag tatatacata cagttaactc aatacagtaa     540
ccaagctatt catctctcct ctccggacgg cgtgaaagta aaactaaccc ctccggtgta     600
aaatattcga ccgaaaacac ctacnggtca ntgtaaaaaa acatatagta ctagtancgc     660
tnataaagga actggtaaaa agatactngt nccaagaaga tttacttgct ggnaatggtt     720
agaaaaatgg caantt                                                    736
```

<210> SEQ ID NO 20
<211> LENGTH: 142
<212> TYPE: PRT
<213> ORGANISM: Triticum aestivum

<400> SEQUENCE: 20

```
Trp Thr Ser Thr Leu Gln Arg Thr Ile Leu Thr Ala Thr Pro Ile Val
1               5                   10                  15

Gly Phe Pro Lys Ile Gln Trp Arg Ala Leu Asp Glu Ile Asn Ser Gly
                20                  25                  30

Val Cys Asp Gly Met Thr Tyr Glu Glu Ile Lys Lys Ile Met Pro Glu
            35                  40                  45

Glu Tyr Glu Ser Arg Lys Lys Asp Lys Leu Arg Tyr Arg Tyr Pro Arg
        50                  55                  60

Gly Glu Ser Tyr Leu Asp Val Ile Gln Arg Leu Glu Pro Val Ile Ile
65                  70                  75                  80

Glu Leu Glu Arg Gln Arg Ala Pro Val Val Ile Ser His Gln Ala
                85                  90                  95

Val Leu Arg Ala Leu Tyr Ser Tyr Phe Ala Asp Arg Pro Leu Arg Glu
            100                 105                 110

Val Pro Asp Met Glu Met Pro Leu His Thr Ile Ile Glu Ile Gln Met
        115                 120                 125

Gly Val Thr Gly Val Glu Glu Lys Arg Tyr Lys Leu Met Asp
    130                 135                 140
```

<210> SEQ ID NO 21
<211> LENGTH: 456
<212> TYPE: PRT
<213> ORGANISM: Saccharomyces cerevisiae

<400> SEQUENCE: 21

```
Met Ser Asp Lys Pro Ile Asp Ile Gln Tyr Asp Lys Gln Ala Thr Pro
1               5                   10                  15
```

-continued

```
Asn Leu Ser Gly Val Ile Thr Pro Thr Asn Glu Thr Gly Asn Asp
             20                  25                  30

Ser Val Arg Glu Lys Leu Ser Lys Leu Val Gly Asp Ala Met Ser Asn
         35                  40                  45

Asn Pro Tyr Phe Ala Ala Gly Gly Leu Met Ile Leu Gly Thr Gly
         50                  55                  60

Leu Ala Val Ala Arg Ser Gly Ile Ile Lys Ala Ser Arg Val Leu Tyr
 65                  70                  75                  80

Arg Gln Met Ile Val Asp Leu Glu Ile Gln Ser Lys Asp Lys Ser Tyr
                 85                  90                  95

Ala Trp Phe Leu Thr Trp Met Ala Lys His Pro Gln Arg Val Ser Arg
             100                 105                 110

His Leu Ser Val Arg Thr Asn Tyr Ile Gln His Asp Asn Gly Ser Val
             115                 120                 125

Ser Thr Lys Phe Ser Leu Val Pro Gly Pro Gly Asn His Trp Ile Arg
         130                 135                 140

Tyr Lys Gly Ala Phe Ile Leu Ile Lys Arg Glu Arg Ser Ala Lys Met
145                 150                 155                 160

Ile Asp Ile Ala Asn Gly Ser Pro Phe Glu Thr Val Thr Leu Thr Thr
                 165                 170                 175

Leu Tyr Arg Asp Lys His Leu Phe Asp Asp Ile Leu Asn Glu Ala Lys
             180                 185                 190

Asp Ile Ala Leu Lys Thr Thr Glu Gly Lys Thr Val Ile Tyr Thr Ser
         195                 200                 205

Phe Gly Pro Glu Trp Arg Lys Phe Gly Gln Pro Lys Ala Lys Arg Met
     210                 215                 220

Leu Pro Ser Val Ile Leu Asp Ser Gly Ile Lys Glu Gly Ile Leu Asp
225                 230                 235                 240

Asp Val Tyr Asp Phe Met Lys Asn Gly Lys Trp Tyr Ser Asp Arg Gly
                 245                 250                 255

Ile Pro Tyr Arg Arg Gly Tyr Leu Leu Tyr Gly Pro Pro Gly Ser Gly
             260                 265                 270

Lys Thr Ser Phe Ile Gln Ala Leu Ala Gly Glu Leu Asp Tyr Asn Ile
         275                 280                 285

Cys Ile Leu Asn Leu Ser Glu Asn Asn Leu Thr Asp Asp Arg Leu Asn
290                 295                 300

His Leu Met Asn Asn Met Pro Glu Arg Ser Ile Leu Leu Leu Glu Asp
305                 310                 315                 320

Ile Asp Ala Ala Phe Asn Lys Arg Ser Gln Thr Gly Glu Gln Gly Phe
                 325                 330                 335

His Ser Ser Val Thr Phe Ser Gly Leu Leu Asn Ala Leu Asp Gly Val
             340                 345                 350

Thr Ser Ser Glu Glu Thr Ile Thr Phe Met Thr Thr Asn His Pro Glu
         355                 360                 365

Lys Leu Asp Ala Ala Ile Met Arg Pro Gly Arg Ile Asp Tyr Lys Val
     370                 375                 380

Phe Val Gly Asn Ala Thr Pro Tyr Gln Val Glu Lys Met Phe Met Lys
385                 390                 395                 400

Phe Tyr Pro Gly Glu Thr Asp Ile Cys Lys Lys Phe Val Asn Ser Val
                 405                 410                 415

Lys Glu Leu Asp Ile Thr Val Ser Thr Ala Gln Leu Gln Gly Leu Phe
             420                 425                 430
```

```
-continued

Val Met Asn Lys Asp Ala Pro His Asp Ala Leu Lys Met Val Ser Ser
        435                 440                 445

Leu Arg Asn Ala Asn His Ile Phe
    450                 455
```